United States Patent
Bricker et al.

(10) Patent No.: US 6,355,852 B1
(45) Date of Patent: *Mar. 12, 2002

(54) SELECTIVE AROMATICS TRANSALKYLATION

(75) Inventors: Maureen L. Bricker, Buffalo Grove; Charles P. McGonegal, Addison, both of IL (US)

(73) Assignee: UOP LLC, Des Plaines, IL (US)

( * ) Notice: Subject to any disclaimer, the term of this patent is extended or adjusted under 35 U.S.C. 154(b) by 52 days.

This patent is subject to a terminal disclaimer.

(21) Appl. No.: 09/780,328

(22) Filed: Feb. 12, 2001

Related U.S. Application Data

(63) Continuation of application No. 09/421,145, filed on Oct. 19, 1999.
(60) Provisional application No. 60/104,763, filed on Oct. 19, 1998.

(51) Int. Cl.$^7$ .................................................. C07C 5/52
(52) U.S. Cl. ...................................... 585/470; 585/475
(58) Field of Search ............................... 585/470, 474, 585/475

(56) References Cited

U.S. PATENT DOCUMENTS

| | | | |
|---|---|---|---|
| 3,597,490 A | 8/1971 | Otani et al. | 260/672 |
| 5,177,286 A | 1/1993 | Hagen et al. | 585/472 |
| 5,516,955 A | 5/1996 | Gentry | 585/477 |
| 5,563,311 A | 10/1996 | Chang et al. | 585/467 |
| 6,005,153 A | 12/1999 | Zinnen et al. | 585/475 |
| 6,008,424 A | 12/1999 | Zinnen et al. | 585/475 |

*Primary Examiner*—Thuan D. Dang
(74) *Attorney, Agent, or Firm*—John G. Tolomei; John F. Spears, Jr.; Michael A. Moore

(57) ABSTRACT

An improved process is disclosed for the selective transalkylation of toluene and, optionally, of $C_9$ aromatics. The process preferably uses a bound sulfated zirconia catalyst to provide improved selectivity for the production of xylenes.

12 Claims, 1 Drawing Sheet

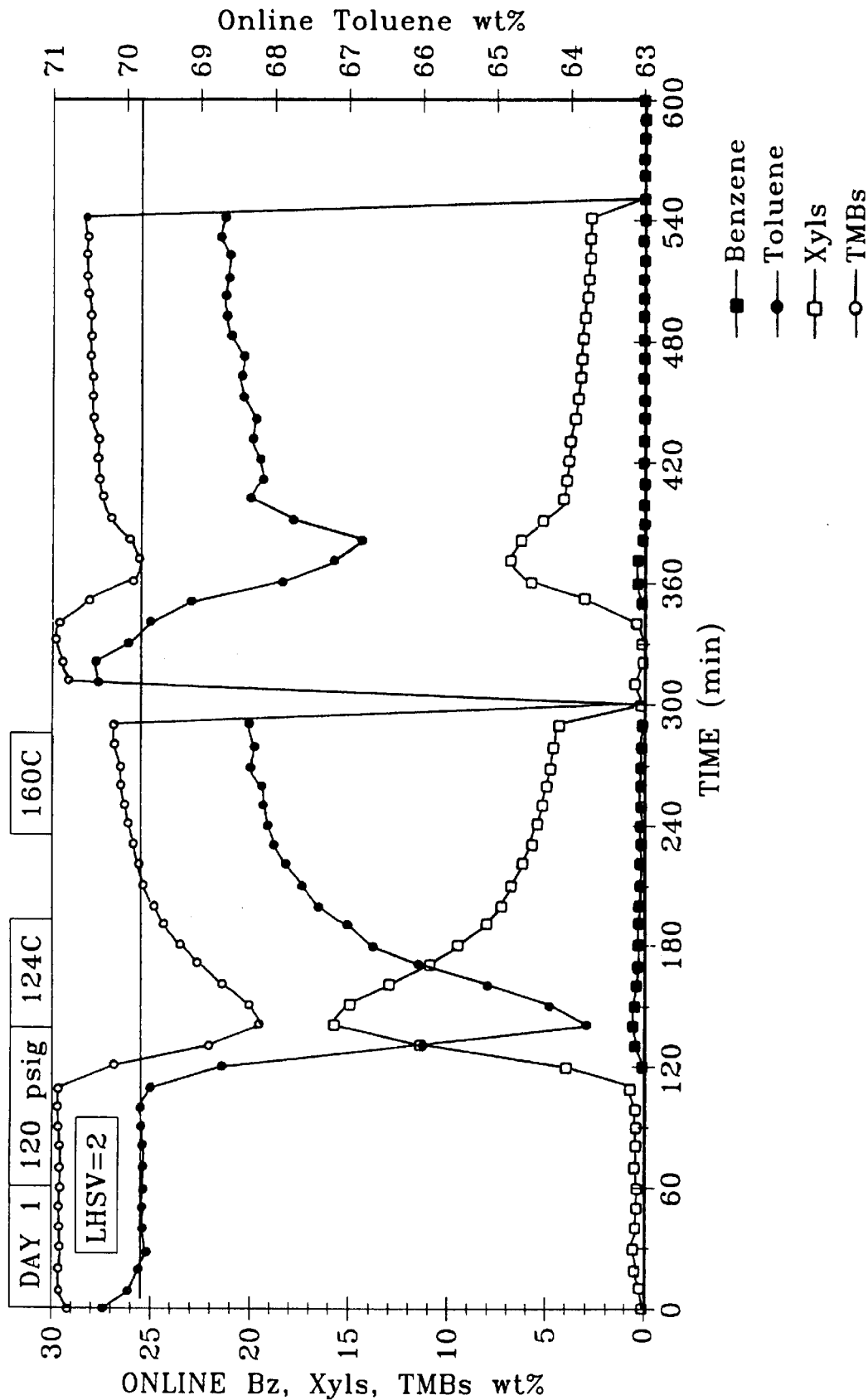

SELECTIVE AROMATICS TRANSALKYLATION

CROSS-REFERENCE TO RELATED APPLICATION

This application is a Continuation of U.S. application Ser. No. 09/421,145, filed on Oct. 19, 1999, now allowed which is incorporated herein by reference in its entirety and which claims the benefit of U.S. Provisional Application No. 60/104,763, filed on Oct. 19, 1998.

BACKGROUND OF THE INVENTION

This invention relates to an improved process for the conversion of aromatic hydrocarbons. More specifically, the present invention concerns disproportionation and transalkylation of aromatic hydrocarbons to obtain xylenes.

The xylene isomers are produced in large volumes from petroleum as feedstocks for a variety of important industrial chemicals. The most important of the xylene isomers is para-xylene, the principal feedstock for polyester which continues to enjoy a high growth rate from large base demand. Orthoxylene is used to produce phthalic anhydride, which has high-volume but mature markets. Meta-xylene is used in lesser but growing volumes for such products as plasticizers, azo dyes and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Often toluene is dealkylated to produce benzene or disproportionated to yield benzene and $C_8$ aromatics from which the individual xylene isomers are recovered.

A current objective of many aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. Benzene produced from transalkylation processes often is not sufficiently pure to be competitive in the market. A higher yield of xylenes at the expense of benzene thus is a favorable objective, and processes to transalkylate $C_9$ aromatics and toluene have been commercialized to obtain high xylene yields.

Such transalkylation processes have been disclosed in the patent literature for some time. U.S. Pat. No. 3,597,490 (Otani et al.) teaches toluene conversion along with 0.5–50 mol percent $C_9$ aromatics using a solid acid catalyst. The reaction is carried out at a temperature of 300° to 650° C. Separation and recycle of xylene isomers also is disclosed.

U.S. Pat. No. 5,177,286 (Hagen et al.) teaches production of p-alkyltoluene via transmethylation with a feed which may comprise toluene and a variety of polymethylbenzenes. The catalyst comprises a Lewis acid and/or Bronsted acid that is more acidic than ferric chloride and at least as acidic as ferric bromide. Operating conditions comprise a temperature of from about −40° to 80° C.

Conventional technology for transalkylation is based on catalysts comprising zeolitic aluminosilicates, believed to be effected via a strong Brönsted acid. A lower-energy path would provide potential for greater selectivity and improved economics.

SUMMARY OF THE INVENTION

It is an object of the present invention to provide an improved process for the transalkylation of aromatic hydrocarbons. A specific objective is obtain a high yield of xylenes by transalkylation of toluene and, optionally, higher aromatics.

This invention is based on the discovery that transalkylation of toluene and $C_9$ aromatics using a sulfated zirconia catalyst shows favorable results at mild conditions.

A broad embodiment of the present invention is directed to a process for the transalkylation of a toluene-containing feedstock to obtain a product comprising para-xylene using a catalyst comprising one or more sulfated oxides and hydroxides of elements of Group IVB (IUPAC 4) of the Periodic Table. The catalyst preferably comprises a refractory inorganic-oxide binder, especially alumina.

The feedstock preferably comprises $C_9$ aromatics which are transalkylated along with toluene to provide a higher yield of $C_8$ aromatics. The transalkylation preferably is effected in the liquid phase at relatively mild conditions, comprising a temperature within the range of about 110° to 250° C.

Mixed $C_8$ aromatics recovered from the transalkylation effluent optionally is sent a xylene-separation zone; preferably, para-xylene is recovered by adsorption.

These as well as other objects and embodiments will become apparent from the detailed description of the invention.

BRIEF DESCRIPTION OF THE DRAWINGS

The FIGURE shows toluene and trimethylbenzene conversion and transalkylation reaction products as a function of temperature.

DESCRIPTION OF THE PREFERRED EMBODIMENTS

The present process is described as a transalkylation process, relating to the exchange of sidechains between aromatic nuclei; this term is generally applied when there is an exchange of sidechains between aromatic species, e.g., toluene and $C_9$ aromatics. The term "transalkylation" is intended herein to embrace the reaction often characterized as disproportionation, usually applied to the reaction of a single hydrocarbon specie.

The feedstock to the present process comprises alkylaromatic hydrocarbons of the general formula $C_6H_{(6-n)}R_n$, where n is an integer from 1 to 5 and R is $CH_3$, $C_2H_5$, $C_3H_7$, or $C_4H_9$, in any combination to obtain more-valuable alkylaromatics. Suitable alkylaromatic hydrocarbons include, for example but without so limiting the invention, benzene, toluene, xylenes, ethylbenzene, trimethylbenzenes, ethyltoluenes, propylbenzenes, tetramethylbenzenes, ethyldimethylbenzenes, diethylbenzenes, methylpropylbenzenes, ethylpropylbenzenes, triethylbenzenes, di-isopropylbenzenes, and mixtures thereof.

The feedstock preferably comprises toluene and suitably is derived from one or a variety of sources. Toluene may be produced synthetically, for example, from naphtha by catalytic reforming or by pyrolysis followed by hydrotreating to yield an aromatics-rich product. The toluene feedstock may be derived from such product with suitable purity by extraction of aromatic hydrocarbons from a mixture of aromatic and nonaromatic hydrocarbons and fractionation of the extract. For instance, aromatics may be recovered from a reformate through the use of a selective solvent, such as one of the sulfolane type, in a liquid-liquid extraction zone. The recovered aromatics may then be separated into streams having the desired carbon number range by fractionation. The feedstock should contain no more than about 10 mass-% nonaromatics; the content of benzene and $C_8$ aromatics is principally an economic decision relating to the efficiency of conversion of toluene to these aromatics. When the severity of reforming or pyrolysis is sufficiently high, extraction may be unnecessary and fractionation may be sufficient to prepare the toluene feedstock.

A preferred component of the feedstock is a heavy-aromatics stream comprising $C_9$ aromatics, thereby effecting transalkylation of toluene and $C_9$ aromatics to yield additional Xylenes. Indan may be present in the heavy-aromatics stream although it is not a desirable component to effect high yields of $C_8$-aromatics product. $C_{10}+$ aromatics also may be present, preferably in an amount of 30% or less of the feed. The heavy-aromatics stream preferably comprises at least about 90 mass-% aromatics, and may be derived from the same or different known refinery and petrochemical processes as the toluene feedstock and/or may be recycled from the separation of the product from transalkylation. Benzene also may be present in the combined feed to transalkylation.

The feedstock, usually in admixture with toluene and/or heavy aromatics recycled from the products of the transalkylation reaction, is preferably transalkylated in the liquid phase and in the absence of hydrogen. If present, free hydrogen is associated with the feedstock and recycled hydrocarbons in an amount of from about 0.01 moles per mole of alkylaromatics up to the hydrogen saturation limit at transalkylation conditions. The transalkylation reaction preferably yields a product having an increased xylene content which usually also comprises benzene, unreacted toluene, and smaller amounts of $C_9+$ aromatics.

The feed to the transalkylation zone usually first is heated by indirect heat exchange against the effluent of the reaction zone and then is heated to reaction temperature by exchange with a warmer stream, steam or a furnace. The feed, preferably in a liquid state, then is passed through a reaction zone which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of an effluent stream comprising unconverted feed and product hydrocarbons. This effluent is normally cooled by indirect heat exchange against the stream entering the reaction zone and then further cooled through the use of air or cooling water. The effluent may be passed into a stripping column in which substantially all $C_5$ and lighter hydrocarbons present in the effluent are concentrated into an overhead stream and removed from the process. An aromatics-rich stream is recovered as net stripper bottoms which is referred to herein as the transalkylation effluent.

Conditions employed in the transalkylation zone of the subject process normally include a temperature of from about 110° to 250° C., and preferably from about 120° to 180° C. Excellent results are obtained at a temperature of from about 130° to 145° C. The temperature required to maintain the desired degree of conversion will increase as the catalyst gradually loses activity during processing.

The transalkylation zone is operated at moderately elevated pressures broadly ranging from about 100 kPa to 6 MPa absolute. A preferred pressure range is from 2 to 3.5 MPa. The transalkylation reaction can be effected over a wide range of space velocities, with higher space velocities effecting a higher ratio of para-xylene at the expense of conversion. Liquid hourly space velocity generally is the range of from about 0.2 to 20 $hr^{-1}$, with a value in the range of from about 1 to 10 $hr^{-1}$ being preferred.

The transalkylation effluent is separated into a light recycle stream, a mixed $C_8$ aromatics product and a heavy-aromatics stream. The $C_8$ aromatics product may be sent to a xylene separation zone for recovery of pure para-xylene and/or, optionally, other xylenes and ethylbenzene. The light recycle stream may be diverted to other uses such as to benzene and toluene recovery, but alternatively is recycled partially to the transalkylation zone since it contains not only benzene and toluene but also amounts of nonaromatics which would remain with the benzene and reduce its commercial value. The heavy recycle stream contains substantially all of the $C_9$ and heavier aromatics and may be partially or totally recycled to the reaction if transalkylation is an objective of the process.

The xylene-separation zone may use any one or several different separation techniques such as fractionation, crystallization or selective adsorption to remove para-xylene from the stream of mixed $C_8$ aromatics which enters the xylene-separation zone. An adsorptive separation zone is preferred containing a bed of molecular sieves operated in accordance with the teaching of U.S. Pat. No. 3,201,491 to simulate the use of a continuously moving bed of molecular sieves. Subsequent improvements to the process are described in U.S. Pat. Nos. 3,696,107 and 3,626,020. The preferred xylene-separation zone is therefore operated at adsorption conditions which include temperatures in the range of from about 30° to 300° C., but preferably from 40° to 250° C. This zone may be operated in either the vapor phase or the liquid phase with liquid-phase operations being preferred. Pressures utilized may vary from atmospheric to 70 atmospheres, with more moderate pressures of from about 5 to 20 atmospheres being preferred. Further details on the operation of the preferred xylene-separation zone may also be obtained from U.S. Pat. Nos. 4,039,599 and 4,184,943 and the previously cited references which concern para-xylene separation. The xylene-separation zone may depart from this preferred mode of operation through the use of batch-type operations or a true moving bed of solid adsorbent. The simulated cocurrent adsorptive separation process of U.S. Pat. No. 4,402,832 may also be employed. The extract and raffinate streams may be handled as described in these references or as described in U.S. Pat. No. 4,381,419.

The skilled routineer will recognize variations in the process combination described above which are within the scope of the invention. For example, benzene as well as toluene may be charged to the transalkylation zone as a supplementary feedstock. The xylene-separation zone may use one or more of several known separation techniques such as adsorption, crystallization and fractionation. Ortho-xylene and/or meta-xylene may be recovered as pure products from the xylene-separation zone.

The process of the present invention utilizes a solid strong-acid catalyst comprising an anion-modified metal oxide. The metal-oxide support comprises at least one oxide, hydroxide, oxyhydroxide or oxide-hydrate of Groups IVB (IUPAC 4), IIIA (IUPAC 13) and IVA (IUPAC 14) metals and iron[See Cotton and Wilkinson, *Advanced Inorganic Chemistry,* John Wiley & Sons (Fifth Edition, 1988)]. The favored form of the support depends upon the metal chosen;

for example, zirconium hydroxide and aluminum oxide are the respective favored forms of these elements. Zirconia and titania are preferred metal-oxide supports, with zirconia being especially preferred.

The anion modifier generally is selected from one or more of sulfate and the oxide, hydroxide, oxyhydroxide or oxide-hydrate of metals of Groups VB (IUPAC 5), VIB (IUPAC 6), VIIB (IUPAC 7), VII (IUPAC 8–10) and VA (IUPAC 15). Sulfate, tungstate and molybdate modifiers are preferred. Favored anion-modified metal oxides are tungstated zirconia and, particularly, sulfated zirconia.

The preferred zirconium oxide or hydroxide is converted via calcination to crystalline form. An anion modifier is composited with the catalyst by any suitable means, for example as a component of an initial slurry preparation along with the Group IVB metal hydroxide or by impregnation before or after calcination of the support. Optionally, the catalyst is bound with a refractory inorganic oxide. The support, sulfate and optional binder may be composited in any order effective to prepare a catalyst useful for the transalkylation of hydrocarbons.

Raw material for the support of the present catalyst may be purchased as a hydroxide of a Group IVB (IUPAC 4) metal. For example, suitable zirconium hydroxide is available from MEI of Flemington, N.J. Alternatively, the hydroxide may be prepared by hydrolyzing metal oxy-anion salt compounds, for example $ZrOCl_2$, $ZrO(NO_3)_2$, $Zr(OH)NO_3$, $ZrOSO_4$, $TiOCl_2$ and the like. The hydrolysis can be effected using a hydrolyzing agent such as ammonium hydroxide, sodium hydroxide, potassium hydroxide, sodium sulfate, $(NH_4)_2HPO_4$ and other such compounds known in the art. The metal oxy-anion salt may in turn be prepared from available materials, for example by treating $ZrOCO_3$ with nitric acid. The hydroxide as purchased or generated by hydrolysis preferably is dried at a temperature of from about 100 to 300° C. to vaporize volatile compounds.

A preferred sulfated support is prepared by treatment with a suitable sulfating agent to form a solid acid, optionally a solid superacid having acid strength or proton-donating ability at least as great as anhydrous sulfuric acid. Sulfate ion is incorporated into a catalytic composite, for example, by treatment with sulfuric acid in a concentration usually of from about 0.01–10N and preferably from about 0.1 5N. Compounds such as hydrogen sulfide, mercaptans or sulfur dioxide, which are capable of forming sulfate ions upon calcining, may be employed as alternative sources. Preferably ammonium sulfate is employed to provide sulfate ion to the catalytic composite. Sulfate is composited with the surface of the support material to form, it is believed without so limiting the invention, a mixture of Brönsted and Lewis acid sites. The sulfur content of the finished catalyst generally is in the range of about 0.5 to 5 mass-%, and preferably is from about 1 to 2.5 mass-%. The sulfated composite is dried, preferably followed by calcination at a temperature of about 500 to 700° C. particularly if the sulfation is to be followed by incorporation of the platinum-group metal.

Preferably the catalytic composition comprises a binder in order to provide catalyst particles in a convenient form according to the present invention. The binder usually comprises from about 2 to 50 mass-%, preferably from about 5 to 20 mass-%, of the finished catalyst. The art teaches that any refractory inorganic oxide binder is suitable. One or more of silica, alumina or magnesia are preferred binder materials of the present invention, with alumina or silica being more preferred among binder materials. The particularly preferred binder material is alumina, with eta- and/or especially gamma-alumina being favored.

The hydroxide and binder may be composited to form particle shapes known to those skilled in the art such as spheres, extrudates, rods, pills, pellets, tablets or granules. A preferred form of carrier material is a cylindrical extrudate, suitably prepared by mixing alumina powder and catalyst carrier with water and suitable peptizing agents such as HCl until an extrudable dough is formed. The amount of water added to form the dough is typically sufficient to give a loss on ignition (LOI) at 500° C. of about 25 to 65 mass-%. The resulting dough is extruded through a suitably sized die to form extrudate particles. These particles are then dried at a temperature of about 260° to about 550° C. for a period of about 0.1 to 5 hours to form the extrudate particles. The preferred diameter of cylindrical extrudate particles is between about 0.7 and 3.5 mm, with a length-to-diameter ratio of between about 1:1 and 5:1.

Alternative spherical particles may be formed directly by the oil-drop method as disclosed hereinbelow or from extrudates by rolling extrudate particles on a spinning disk. Manufacture of spheres by the well known continuous oil-drop method comprises: forming an alumina hydrosol by any of the techniques taught in the art and converting the alumina hydrogel to the corresponding crystalline gamma-alumina. U.S. Pat. No. 2,620,314 provides details and is incorporated herein by reference thereto.

A catalyst support useful in the process of the invention may incorporate other porous, adsorptive, high-surface-area materials. Within the scope of the present invention are refractory supports containing one or more of: (1) other refractory inorganic oxides such as titania, magnesia, zirconia, chromia, thoria, boria or mixtures thereof, (2) synthetically prepared or naturally occurring clays and silicates, which may be acid-treated; (3) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations; (4) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; (5) spinels such as $MgAl_2O_4$, $FeAl_2O_4$, $ZnAl_2O_4$; and (6) combinations of materials from one or more of these groups. Preferably, however, the solid strong-acid catalyst consists essentially of sulfated zirconia and an inorganic-oxide binder.

During processing the catalyst gradually loses transalkylation activity, as evidenced by the need to gradually increase operating temperature in order to maintain conversion; the catalyst eventually must be replaced or reactivated. Typically a deactivated catalyst comprises carbon accumulated during processing.

Optionally, therefore, a deactivated catalyst is reactivated to restore transalkylation activity. Reactivation or regeneration may be effected by any means known in the art including decoking, oxidation, oxychlorination and/or treatment with an inert gas or hydrogen. Preferably a catalyst is reactivated by contacting with a liquid hydrocarbon stream. The reactivation temperature is selected to effect catalyst reactivation in a minimum time consistent with maintenance of a liquid hydrocarbon reactivation stream and the capabilities (e.g., operating pressure) of the transalkylation process unit, and preferably is within the ranges specified previously for operating temperature, i.e., from about 110° C. to 250° C. Generally free hydrogen is associated with the liquid hydrocarbon stream in an amount of from about 0.01 moles per mole of $C_5+$ hydrocarbons to the hydrogen saturation limit at reactivation conditions. Reactivation conditions usually also comprise a pressure of from 300 kPa to 4 MPa and liquid hourly space velocity of from 0.5 to 15 $hr^{-1}$.

The liquid hydrocarbon reactivation stream preferably comprises feedstock to the present transalkylation process as described hereinabove, although the reactivation stream may comprise transalkylated product, an intermediate stream in the transalkylation process, or another convenient hydrocarbon stream. Preferably the reactivation stream is an alkylaromatic stream as described hereinabove. A spent reactivation stream which has been passed over the deactivated catalyst may be blended into finished fuel products or sent to further processing in a refinery.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art will recognize, which are within the spirit of the invention.

Example I

A transalkylation catalyst was prepared in order to illustrate the benefits of the invention. $Zr(OH)_4$ prepared by neutralizing $Zr(NO_3)_2$ with ammonia was spray-impregnated with a solution of $(NH_4)_2SO_4$, dried at 120° C. and 300° C., then calcined at 650° C.

Example II

The catalyst of Example I was tested for transalkylation activity and selectivity. The feedstock was a mixture of 70 mass-% toluene and 30 mass-% 1,2,4-trimethylbenzene. Operating conditions comprised a pressure of about 900 kPa, liquid hourly space velocity of 2.0 $hr^{-1}$ and temperatures varying in a from 124° to 160° C. The reaction was carried out in the liquid phase without the presence of added hydrogen.

The results of the tests are shown in the Figure. FIG. 1 is a plot of activity, shown as toluene and trimethylbenzene conversion, and selectivity shown as xylene yield. Temperature was ramped up from 124° to 160° C. at about 120 minutes, and the test was briefly halted at about 300 minutes.

The catalyst showed essentially no transalkylation activity at 124° C., but xylenes were produced at 160° C.

We claim:

1. A process for the transalkylation of a toluene-containing feedstock comprising contacting the feedstock in liquid phase with a catalyst comprising one or more sulfated oxides and sulfated hydroxides of elements of Group IVB (IUPAC 4) of the Periodic Table at transalkylation conditions comprising a temperature of from about 110° to 250° C., a pressure of from about 100 kPa to 6 MPa absolute, and a liquid hourly space velocity of from about 0.2 to 20 $hr^{-1}$ and the absence of added free hydrogen to obtain a transalkylation effluent containing xylenes.

2. A process for the transalkylation of a toluene-containing feedstock comprising contacting the feedstock in liquid phase with a catalyst comprising one or more sulfated oxides and sulfated hydroxides of elements of Group IVB (IUPAC 4) of the Periodic Table and a refractory inorganic oxide at transalkylation conditions comprising a temperature of from about 110° to 250° C., a pressure of from about 100 kPa to 6 MPa absolute, and a liquid hourly space velocity of from about 0.2 to 20 $hr^{-1}$ to obtain a transalkylation effluent containing xylenes.

3. The process of claim 2 wherein the refractory inorganic oxide is alumina.

4. A process for the transalkylation of a toluene-containing feedstock comprising contacting the feedstock in liquid phase with a catalyst consisting essentially of one or more of the sulfated oxides and sulfated hydroxides of elements of Group IVB (IUPAC 4) of the Periodic Table and a refractory inorganic oxide at transalkylation conditions comprising a temperature of from about 110° to 250° C., a pressure of from about 100 kPa to 6 MPa absolute, and a liquid hourly space velocity of from about 0.2 to 20 $hr^{-1}$ to obtain a transalkylation effluent containing xylenes.

5. A process for the transalkylation of a toluene-containing feedstock comprising contacting the feedstock in liquid phase with a catalyst comprising one or more sulfated oxides and sulfated hydroxides of elements of Group IVB (IUPAC 4) of the Periodic Table at transalkylation conditions comprising a temperature of from about 110° to 250° C., a pressure of from about 100 kPa to 6 MPa absolute, and a liquid hourly space velocity of from about 0.2 to 20 $hr^{-1}$ to obtain a transalkylation effluent containing xylenes and contacting a deactivated catalyst with a liquid-phase hydrocarbon stream at reactivation conditions to obtain a reactivated catalyst and re-utilizing the reactivated catalyst in the transalkylation process.

6. A process for the transalkylation of a feedstock containing toluene and $C_9$ aromatics comprising contacting the feedstock in liquid phase with a catalyst consisting essentially of a sulfated support comprising one or more of the sulfated oxides and sulfated hydroxides of elements of Group IVB (IUPAC 4) of the Periodic Table and a refractory inorganic oxide at transalkylation conditions comprising a temperature of from about 110° to 250° C., a pressure of from about 100 kPa to 6 MPa absolute, and a liquid hourly space velocity of from about 0.2 to 20 $hr^{-1}$ to obtain a transalkylation effluent containing xylenes.

7. The process of claim 6 wherein the transalkylation conditions comprise a temperature of from about 120° to 180° C.

8. The process of claim 7 wherein the transalkylation conditions comprise a temperature of from about 130° to 145° C.

9. The process of claim 6 comprising effecting transalkylation in the absence of added free hydrogen.

10. The process of claim 6 further comprising recovering para-xylene from the transalkylation effluent in a xylene-separation zone.

11. The process of claim 6 further comprising contacting a deactivated catalyst with a liquid-phase hydrocarbon stream at reactivation conditions to obtain a reactivated catalyst and re-utilizing the reactivated catalyst in the transalkylation process.

12. The process of claim 6 further characterized in that the $C_9$ aromatics comprise trimethylbenzene.

* * * * *